US006818672B1

(12) United States Patent
Bologna et al.

(10) Patent No.: US 6,818,672 B1
(45) Date of Patent: Nov. 16, 2004

(54) TREATING ENDOMETRIOSIS OR INFERTILITY, OR IMPROVING FERTILITY

(75) Inventors: William J. Bologna, Paris (FR); Dominique De Ziegler, Paris (FR); Howard L. Levine, Oceanside, NY (US)

(73) Assignee: Columbia Laboratories, Inc., Livingston, NJ (US)

( * ) Notice: Subject to any disclaimer, the term of this patent is extended or adjusted under 35 U.S.C. 154(b) by 9 days.

(21) Appl. No.: 10/089,796

(22) PCT Filed: Oct. 4, 2000

(86) PCT No.: PCT/EP00/09708

§ 371 (c)(1),
(2), (4) Date: Jul. 24, 2002

(87) PCT Pub. No.: WO01/24788

PCT Pub. Date: Apr. 12, 2001

Related U.S. Application Data
(60) Provisional application No. 60/157,754, filed on Oct. 5, 1999.

(51) Int. Cl.$^7$ .................... A01N 33/02; A61K 31/135
(52) U.S. Cl. .................. 514/653; 514/654; 514/967; 424/430; 424/433; 424/434
(58) Field of Search ................... 424/486, 430, 424/434, 433; 514/653, 654, 967

(56) References Cited

U.S. PATENT DOCUMENTS

| | | | |
|---|---|---|---|
| 4,615,697 A | | 10/1986 | Robinson ................. 604/890 |
| 5,667,492 A | | 9/1997 | Bologna et al. ........... 604/57 |
| 6,126,959 A | * | 10/2000 | Levine et al. ............. 424/434 |
| 6,180,355 B1 | | 1/2001 | Alexander et al. ......... 435/7.1 |
| 6,197,327 B1 | * | 3/2001 | Harrison et al. .......... 424/430 |
| 6,207,696 B1 | * | 3/2001 | Peterson et al. .......... 514/400 |
| 6,211,221 B1 | | 4/2001 | Peterson et al. .......... 514/399 |

FOREIGN PATENT DOCUMENTS

| | | |
|---|---|---|
| WO | 93/02662 A | 2/1993 |
| WO | 99/13862 A | 3/1999 |

OTHER PUBLICATIONS

E.K. Lang, Organic vs Functional Obstructionof the Fallopian Tubes: Differentiation with Prostaglandin Antagonist and Beta 2 Agonist–Mediated Hysterosalpingography and Selective Ostial Salpingography, 1991, American Roentgen Ray Society, vol. 157 pp 77–80.*
Database Biosis Online; Biosciences Information Service, Philadelphia, PA, US; 1991, Lang E K; "Organic vs. Functional Obstruction of the Fallopian Tubes Differentiation with Prostaglandin Antagonist–Mediated Hysterosalpingography and Selective Ostail Salpingography"; Database Accession No. PREV199192058871; XP002168612.

John A. Sampson, M.D., *Peritoneal Endometriosis Due To The Menstrual Dissemination Of Endometrial Tissue Into The Peritoneal Cavity*, The American Journal of Obstetrics and Gynecology, vol. XIV, Jul.–Dec., 1927, pp. 422–469.
R.A. Woodbury, M.D., Ph.D., Richard Torpin, M.D., George P. Child, Ph.D., Henry Watson, M.D. and Marie Jarboe, M.D., *Myometrial Physiology and its Relation to Pelvic Pain* J.A.M.A., Jul. 26, 1947, pp. 1081–1085.
Manuel Martinez–Gaudio, M.d., Toshiro Yoshida, M.D., Lars Philip Bengtsson, M.D., *Propagated and nonpropagated myometrial contractions in normal menstrual cycles*, The American Journal of Obstetrics and Gynecology, vol. 115, No. 1, Jan. 1, 1973, pp. 107–111.
M. Akerlund, K.E. Andersson and I. Ingemarsson, *Effects Of Terbutaline On Myometrial Activity, Uterine Blood Flow, and Lower Abdominal Pain In Women With Primary Dysmenorrhoea*, British Journal of Obstetrics and Gynaecology, Sep., 1976, vol. 83, No. 9, pp. 673–678.
Robert L. Barbieri, M.D., *CA–125 in patients with endometriosis*, Fertility and Sterility, vol. 45, No. 6, Jun., 1986, pp. 767–769.
Wolfgang Jäger, M.D., Christiane Meier, M.D., Ludwig Wildt, M.D., Willi Sauerbrei, M.D., Norbert Lang, M.D., *CA–125 serum concentrations during the menstrual cycle*, Fertility and Sterility, vol. 50, No. 2, Aug., 1988, pp. 223–227.
Jacques S. Abramowicz, M.D., David F. Archer, M.D., *Uterine endometrial peristalsis—a transvaginal ultrasound study*, Fertility and Sterility, vol. 54, No. 3, Sep., 1990, pp. 451–454.
Mark D. Hornstein, M.D., Phaedra P. Thomas, R.N., Ray E. Gleason, Ph.D. and Robert L. Barbieri, M.D., *Menstrual cyclicity of CA–125 in patients with endometriosis*, Fertility and Sterility, vol. 58, No. 2, Aug., 1992, pp. 279–283.
Clarence Wilbur Taber, *Taber's Cyclopedic Medical Dictionary*, 17th ed., 1993, p. 592.
Alberto Salamanca, M.D., Estanislao Beltrán, M.D., *Subendometrial contractility in menstrual phase visualized by transvaginal sonography in patients with endometriosis*, Fertility and Sterility, vol. 64, No. 1, Jul. 1995, pp. 193–195.
G. Kunz, D. Beil, H. Deininger, L. Wildt and G. Leyendecker, *The dynamics of rapid sperm transport through the female genital tract; evidence from vaginal sonography of uterine peristalsis and hysterosalpingoscintigraphy*, Human Reproduction vol. 11, No. 3, 1996, pp. 627–632.

(List continued on next page.)

Primary Examiner—Gary Kunz
Assistant Examiner—Konata M. George
(74) Attorney, Agent, or Firm—Winston & Strawn LLP

(57) ABSTRACT

The present invention concerns compositions and methods for using a β-adrenergic agonist for treating endometriosis, for treating infertility, and for improving fertility. The present invention further concerns formulating such a composition or method in such a way as to provide therapeutically sufficient levels of the β-adrenergic agonist locally while avoiding adverse systematic concentrations in the host, thereby minimizing or avoiding adverse side effects.

23 Claims, No Drawings

OTHER PUBLICATIONS

G. Leyendecker, G. Kunz, L. Wildt, D. Beil and H. Deininger, *Uterine hyperperistalsis and dysperistalsis as dysfunctions of the mechanism of rapid sperm transport in patients with endometriosis and infertility,* Human Reproduction vol. 11, No. 7, 1996, pp. 1542–1551.

Marga M. IJland, Johannes L. H. Evers, Gerard A. J. Dunselman, Henk J. Hoogland, *Subendometrial contractions in the nonpregnant uterus: an ultrasound study,* European Journal of Obstetrics and Gynecology and Reproductive Biology, 70, Dec., 1996, pp. 23–24.

Louis Sanford Goodman, Alfred Gilman, Goodman and Gilman's *The Pharmacological Basis of Therapeutics,* 9th ed., 1996, p. 946.

Marga M. IJland, M.D., Henk J. Hoogland, M.D., A. J. Dunselman, M.D., Cornelia R. Lo, M.D. and Johannes L. H. Evers, M.D., *Endometrial wave direction switch and the outcome of in vitro fertilization,* Fertility and Sterility, vol. 71, No. 3, Mar., 1999, pp. 476–481.

* cited by examiner

TREATING ENDOMETRIOSIS OR INFERTILITY, OR IMPROVING FERTILITY

This application is a 371 of PCT/EP00/09708 filed Oct. 4, 2000 which claims priority to Ser. No. 09/668,384 filed Sep. 25, 2000 and which claim the benefit of 60/157,754 filed Oct. 5, 1999.

FIELD OF THE INVENTION

This invention relates to a pharmaceutical composition and to a method for the local administration thereof for the purpose of treating endometriosis, treating infertility, and improving fertility.

BACKGROUND OF THE INVENTION

Endometriosis is a condition in which tissue identical with or resembling the lining of the uterus is present in abnormal places, i.e., outside the uterus. Mainly affecting gynecological and other lower pelvic organs, endometriosis often is accompanied by symptoms of painful uterine cramping (dysmenorrhea), pelvic pain, and infertility. The relatively low incidence of endometriosis, the completely unknown time course of its development, and the invasive nature of diagnostic procedures together present a difficult landscape for studying possible prevention of endometriosis.

Classic treatments of endometriosis have been shown to result in a significant decrease in the size (but not disappearance) of endometriotic lesions and in reduction of pain; however, these treatments typically attempt to mimic either menopause or pregnancy, thereby also blocking ovulation. Because traditional treatments of endometriosis consequently prevent pregnancy by blocking ovulation, it would be a great benefit to be able to use treatments that do not interfere with the normal menstrual cycle.

The menstrual cycle can be divided into three characteristic phases based on uterine contractility: the early follicular phase, the late follicular phase, and the luteal phase. During the early follicular phase, uterine contractions are predominately antegrade, propagating from the fundus to the cervical end of the uterus. This pattern of contractility is instrumental for the forward emptying of uterine content (menses). At this phase of the menstrual cycle, uterine contractions typically are perceived by the female and may present a miniature replica of the expulsive contractions of labor. On occasion, these uterine contractions can become so painful as to interfere with daily routines, perhaps requiring medication and/or time off from regular daily obligations. Such painful contractions are termed dysmenorrhea.

The late follicular phase is characterized by predominately retrograde (cervix to uterus) contractions. These play a role in the rapid transport of sperm from the cervical area to the distal end of the tubes where fertilization takes place. Contractions during the late follicular phase are notoriously painless.

The luteal phase is signified by progesterone-induced uteroquiescence with possibly low-amplitude, bi-directional contractions that originate from both ends of the uterus and meet in the middle area. These bi-directional contractions may help in properly positioning the developing embryo in the mid-section of the uterine cavity, where implantation is most likely to take place.

Recent studies have linked endometriosis with dyskinetic patterns of uterine contractility during the female menstrual cycle. Salamanca, A., Beltran, E., *Subendometrial Contractility in Menstrual Phase Visualized by Transvaginal Sonography in Patients with Endometriosis. Fertil. Steril.*, 65:193–95 (1995). Analogy to other forms of smooth muscle dyskinesia (such as irritable bowel syndrome) suggests that alteration of uterine contractility associated with endometriosis is hyperkinetic in type. Sanfilippo, J. S., Wakim, N. G., Schikler, K. N., Yussman, M. A., *Endometriosis in association with uterine anomaly, Am. J Obstet. Gynecol.* 1986; 154:39–43.

Specifically, hyperkinetic uterine contractions associated with endometriosis may impede the proper antegrade emptying of menstrual blood that normally occurs during the early follicular phase of the menstrual cycle. Normally, menstrual blood empties from the uterus in the direction of the vagina; however, abnormal uterine contractions may cause menstrual blood to chaotically exit the uterus through all openings, including the Fallopian tubes (due to the high-pressure environment of the uterine cavity). This would result in an increase in retrograde bleeding. Retrograde bleeding would ultimately be one of the factors fueling the development of endometriotic implants through direct seeding with debris of endometrial tissue and activation of a chronic inflammatory reaction.

Although it is believed that all women experience some degree of retrograde bleeding during menses (i.e., during the early follicular cycle) at least some of the time. Halme, J., Hammond, M. G., Hulka, J. F., Raj, S. G., Talbert, L. M., *Retrograde menstruation in healthy women and in patients with endometriosis, J. Am Ass. Gynecol. Laparoscopists* 3 [4 Suppl], S5. 1996, a recent study showed that women suffering from endometriosis had more endometrial debris that displayed a stronger disposition to grow in culture than that obtained from women unaffected by endometriosis. Bulletti, D., Rossi, S., Albonetti, A., Polli, V., De Ziegler, D., Massonneau, M., et. al., *Uterine contractility in patients with endometriosis. J. Am. Ass. Gynecol Laparoscopists* 3 [4 Supp.], S5, 1996. Another study showed more extensive retrograde transport toward the uterus and tubes of macroalbumin aggregates labeled with Tc-99 (technitium) and placed in the vaginal formix in women with documented endometriosis as compared to unaffected women. Leyendecker, G., Kunz, G., Wildt, L., Beil D., Deininger H., *Uterine hyperperistalsis and dysperistalsis as dysfunctions of the mechanism of rapid sperm transport in patients with endometriosis and infertility, Hum. Reprod.* 1996; 11:1542–51.

Further, alterations of normal retrograde contractions during the late follicular cycle would seem to affect the rapid transport of sperm and affect fertility. This is because contractility along the female tract (uterus and tubes) appears to be the primary motor assuring the rapid transport of sperm from the cervical area to the distal end of tubes where fertilization takes place. Studies show that sperm have been found in the pelvic cavity within minutes of intercourse, well before it could have traveled there on its own steam, thus implicating retrograde uterine contractility in the rapid transport of sperm. Kunz, G., Beil, D., Deininger, H., Wildt, L., Leyendecker, G., *The dynamics of rapid sperm transport through the female genitalia tract: evidence from vaginal sonography of uterine peristalsis and hysterosalpingoscintigraphy. Hum. Reprod.* 1996; 11:627–32.

β-adrenergic agonists, including, for example, terbutaline, are known to inhibit smooth muscle contractility. Terbutaline and other β-adrenergic agonists exert their pharmacological effects by activation of adenyl cyclase, the enzyme that catalyzes the conversion of adenosine triphosphate (ATP) to cyclic adenosine monophosphate (cAMP). Activation of adenyl cyclase by β-adrenergic agonists increases intracellular levels of cAMP. Cyclic AMP in turn reduces the availability of intracellular free $Ca^{2+}$, which is required for the activation of myosin light-chain kinase, the enzyme that phosphorylates myosin and thereby allows it to combine with actin to form actomyosin. Lack of $Ca^{2+}$ results in disruption of the actin-myosin interaction, with resultant inhibition of smooth muscle contractility.

Terbutaline typically is used as a bronchodilator, and has been approved, for example by the United States Food and Drug Administration, for the treatment of asthma. Oral and intravenous terbutaline also have been used as reasonably effective therapies for preterm labor by stopping contractions or postponing delivery. Lyrenas, S., Grahnen, A., Lindberg, B., et. al., *Pharmacokinetics of Terbutaline During Pregnancy, Eur. J. Clin. Pharmacol.,* 29:619–623 (1986); Berg., G., Lindberg C., Ryden G., *Terbutaline in the Treatment of Preterm Labour, Eur. J. Respir. Dis.,* 65:219–230 (1984).

The use of terbutaline in the treatment of dysmenorrhea has been documented. In one study, terbutaline was shown to inhibit myometrial activity, increase blood flow to the uterus, and relieve the pain occurring during uterine contractions accompanying dysmenorrhea. Akerlund, M., Andersson, K. E., and Ingemarsson, E., *Effects of Terbutaline on Myometrial Activity, Uterine Blood Flow, and Lower Abdominal Pain in Women with Primary Dysmenorrhoea, Br. J. of Obstet. & Gyn.,* 83(9): 673–78 (1976). Kullander, S., Svanberg, L., *Terbutaline Inhalation for Alleviation of Severe Pain in Essential Dysmenorrhea, Acta Obstet. Gynecol. Scand.,* 60:425–27 (1981). Although this therapy did provide some efficacy, the treatment was not sufficient for most patients, who had to supplement with other medications for adequate relief. Further, the effect of each spray lasted as little as 1 hour. Id.

Further, using terbutaline and other β-adrenergic agonists for prevention or treatment of dysmenorrhea or premature labor without the normally-expected side effects has been disclosed in Levine, et. al., U.S. Pat. No. 6,126,959. These side effects are discussed further below.

Shortcomings associated with the therapeutic use of β-adrenergic agonists such as terbutaline have limited their utility. For example, they exhibit low bioavailability after oral administration. Although easily absorbed, β-adrenergic agonists exhibit extensive first-pass sulphation. Bioavailability has been estimated at only between 15 and 20%. Concomitant food intake additionally decreases bioavailability by a further 30%. *Bricanyl: Scientific brochure, Astra France Laboratories* (1993).

Additionally, therapeutic uses of terbutaline have produced significant adverse side effects in the patient, as mentioned above, especially with respect to the cardiovascular system. As a sympathomimetic amine, terbutaline can cause problems in patients with cardiovascular disorders, including arrhythmia, coronary insufficiency, and hypertension. Intravenous administration of terbutaline has been associated with palpitations and peripheral tremors. Åkerlund, M., Andersson, K. F., Ingemarsson, I., *Effects of Terbutaline on Myometrial Activity, Uterine Blood Flow and Lower Abdominal Pain in Women With Primary Dysmenorrhea. Br. J. Obstet., Gyncol.,* 83:673–78 (1976). In addition, intravenous terbutaline has been reported to aggravate pre-existing diabetes and ketoacidosis. Terbutaline also may be problematic for patients with hyperthyroidism, diabetes mellitus, or a history of seizures. Other adverse events include tremors, nervousness, increased heart rate, and diziness. Less frequent adverse effects include headaches, drowsiness, vomiting, nausea, sweating, muscle cramps, and ECG changes. Thus, despite its efficacy, such treatments are often contra-indicated due to the potential adverse consequences—except when administered as discussed in U.S. Pat. No. 6,126,959, cited above.

SUMMARY OF THE INVENTION

The present invention relates to a pharmaceutical composition comprising of (i) a therapeutically effective amount of a β-adrenergic agonist for the purpose of treating endometriosis or infertility, or for improving fertility; and (ii) a pharmaceutically acceptable bioadhesive carrier.

The present invention also relates to a method of treating endometriosis or infertility, or for improving fertility, comprising administering a therapeutically effective amount of a composition comprising a β-adrenergic agonist and a pharmaceutically acceptable bioadhesive carrier locally to the vaginal mucosa of a patient in need thereof.

The present invention also relates to a method of treating endometriosis or infertility, or for improving fertility, comprising administering a therapeutically effective amount of a composition comprising a β-adrenergic agonist without producing detrimental blood levels of the β-adrenergic agonist.

DETAILED DESCRIPTION OF THE INVENTION

Definitions

"Improving fertility" includes, without limitation, increasing the rate of conception or the fertility in a female subject.

"Therapeutically effective amount" refers to the amount required to produce the desired effect.

"Treating endometriosis" refers to:

(i) preventing endometriosis in a female subject that may be predisposed to endometriosis but have not yet been diagnosed with it;

(ii) inhibiting endometriosis, i.e., arresting its development; and/or (iii) relieving endometriosis, i.e., causing its regression.

"Treating infertility" includes, without limitation, alleviating infertility, increasing the rate of conception, or improving fertility in a female subject with decreased or impaired fertility or with recognized infertility.

"Patient" refers to a person who is under medical care or treatment.

"Vaginal mucosa" refers to the vaginal mucous membrane.

Pharmaceutical Composition of the Present Invention

The present invention relates to a pharmaceutical composition comprising of (i) a therapeutically effective amount of a β-adrenergic agonist for the purpose of treating endometriosis, treating fertility, and/or improving fertility; and (ii) a pharmaceutically acceptable bioadhesive carrier, producing efficacy without detrimental blood levels of the β-adrenergic agonist.

β-adrenergic agonists include, without limitation, terbutaline, ritodrine, isoxsuprine, fenoterol, salbutamol, hexoprenaline, metaproterenol, bitolterol, and pirbuterol.

Preferably, the β-adrenergic agonist is terbutaline. The chemical formula of terbutaline is 5-[2-[(1,1-dimethylethyl) amino]-1-hydroxyethyl]-1,3-benzenediol. Its structural formula is as follows:

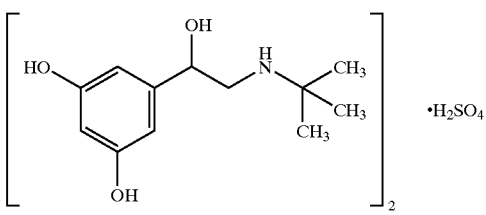

The exact mechanism of β-adrenergic agonist's effect on endometriosis, infertility, and fertility is not known, although it is generally thought to act as a uterine smooth muscle relaxant. It is believed that β-adrenergic agonists normalize hyperactive/dyskinetic uterine activity without altering the proper contractile patterns normally occurring during the menstrual cycle. By normalizing dysfunctional uterine contractions, β-adrenergic agonist is expected to decrease pelvic inflammation and pain by decreasing the retrograde bleeding which is thought to contribute to the development of endometriosis. The β-adrenergic agonist's effect on retrograde bleeding can be measured by monitoring levels of CA-125 (Cancer Antigen-125). Normally, CA-125 levels increase during menstruation; however, this increase is even more pronounced in the case of endometriosis. β-adrenergic agonist is believed to reduce the increase in CA-125 levels during menses.

It further is anticipated that β-adrenergic agonists treat infertility associated with endometriosis, even when the visible expression of endometriosis is mild to moderate. Although the exact mechanism of this effect is unknown, it is expected that normalizing retrograde contractions will improve the rapid transport of sperm from the cervical area to the distal end of the tubes where fertilization takes place. Retrograde transport at mid-cycle was evidenced by visualization of retrograde (vaginal to tubal) displacement of Tc-99-labeled macro-albumin aggregates, a technique referred to as hysterosalpingoscintigraphy (HSS).

Additionally, it is expected that β-adrenergic agonists can improve fertility, even in women with no recognized infertility (i.e., women having only a mild degree of uterine dyskinesia, previously recognized or not). Although the exact mechanism of this effect is unknown, in women presenting with uterine dyskinesia, it is believed that terbutaline will improve uterine contractility, thus improving the rapid transport of sperm from the cervical area to the distal end of the tubes where fertilization takes place.

It is fuirther expected that any of these indications can be accomplished while avoiding the normally-expected detrimental blood levels of the β-adrenergic agonist.

Further, β-adrenergic agonists offer an advantage over classic treatments of endometriosis in that they do not block ovulation.

A pharmaceutically acceptable bioadhesive carrier is a water-insoluble. water-swellable, bioadhesive cross-linked polycarboxylic acid polymer.

The use of such a polycarboxylic acid polymer bioadhesive carrier in combination with a β-adrenergic agonist offers several advantages over the use of the β-adrenergic agonist alone or with other formulations. Upon administration, such a bioadhesive carrier provides a controlled and prolonged release of a β-adrenergic agonist through the vaginal mucosa. By releasing the β-adrenergic agonist directly and locally through the vaginal mucosa, a relatively reduced but focused concentration of a β-adrenergic agonist is administered. Thus, the systemic concentration of β-adrenergic agonist is reduced, resulting in a decrease in many of the significant side effects associated with first-pass metabolism pathways.

Further, the bioadhesive carrier may be presented in any pharmaceutically acceptable form, including a gel, a cream, a tablet, a pill, a capsule, a suppository, a film, or any other pharmaceutically acceptable form that will adhere to the vaginal mucosa. Because the bioadhesive quality of the present invention prevents the β-adrenergic agonist from being diluted or washed away, the β-adrenergic agonist may be administered effectively, even during menses.

The basic drug delivery system formulation of the present invention—the bioadhesive, water-insoluble water-swellable cross-linked polycarboxylic acid polymer formulation to which is added the β-adrenergic agonist—is generally described in U.S. Pat. No. 4,615,697 to Robinson (hereinafter "the '697 patent"), which is incorporated herein by reference.

At least eighty percent of the monomers of which the polymer is comprised should contain at least one carboxyl functionality. The cross-linking agent must be present at such an amount as to provide sufficient bioadhesion and water insolubility. These characteristics allow the system to remain attached to the target epithelial surfaces for a sufficient time to allow the desired dosing to take place.

This level of bioadhesion is usually attained when the cross-linking agent is present at about 0.1 to 6.0 weight percent of the polymer. More preferably, the cross-linking agent is present at about 1.0 to 2.0 weight percent of the polymer. Suitable cross-linking agents include, among others, divinyl glycol, divinylbenzene, N,N-diallylacrylamide, 3,4-dihydroxy-1,5-hexadiene, 2,5-dimethyl-1,5-hexadiene, and other similar agents. Adhesive strengths may be measured by commercially available surface tensiometers.

A preferred polymer for use herein is Polycarbophil. Polycarbophil U.S.P. is commercially available from B.F. Goodrich Specialty Polymers of Cleveland, Ohio, under the trade name NOVEON®-AA1. Polycarbophil is a polyacrylic acid that is cross-linked with divinyl glycol. *The United States Pharmacopeia,* 1995 edition, United States Pharmacopeial Convention. Inc., Rockville, Md., at pages 1240–41.

Polycarbophil has been used in other drug delivery systems. For example, polycarbophil is a main ingredient in the REPLENS® brand vaginal moisturizer. It has also been used as a base for compositions with other active substances such as progesterone (CRINONE® brand topical progesterone preparation) (see U.S. Pat. No. 5,543,150) and Nonoxynol-9 (ADVANTAGE-S® brand contraceptive gel) (see U.S. Pat. No. 5,667,492).

Other useful bioadhesive polymers that may be used in the inventive composition are mentioned in the '697 patent. For example, these include polyacrylic acid polymers cross-linked with 3,4-dihydroxy-1,5-hexadiene, and polymethacrylic acid polymers cross-linked with divinyl benzene. These polymers should not be used in their salt form because this would decrease their bioadhesive capability. These bioadhesive polymers may be prepared by conventional free radical polymerization techniques known to a skilled artisan, i.e., by utilizing initiators such as benzoyl peroxide and azobisisobutyronitrile. Exemplary methods of preparing useful bioadhesives are also disclosed in the '697 patent.

Additionally, any one or more of the additives taught in the '697 patent may be mixed in with the cross-linked polymer in the formulation for maximum efficacy of the drug delivery system or for the comfort of the patient. Such additives may include, among others, lubricants, plasticizing agents, preservatives, gel formers, tablet formers, pill formers, suppository formers, film formers, cream formers, disintegrating agents, coatings, binders, vehicles, coloring agents, taste controlling agents, odor controlling agents, humectants, viscosity controlling agents, and pH-adjusting agents. The present invention contemplates other additives known to an ordinarily skilled artisan.

A preferred embodiment of the inventive composition, COL-2301, comprises the following ingredients:

TABLE 1

COL-2301

| Active Ingredient mg/g | 1.0 | 2.0 | 4.0 |
|---|---|---|---|
| Terbutaline (sulfate) % (w/w) | 0.1% | 0.2% | 0.4% |
| Purified Water | 755.4 | 754.4 | 752.4 |
| Glycerin | 139.0 | 139.0 | 139.0 |
| Light liquid paraffin | 42.0 | 42.0 | 42.0 |
| Carbomer 934P | 30.0 | 30.0 | 30.0 |
| Polycarbophil | 20.0 | 20.0 | 20.0 |
| Methylparaben | 1.8 | 1.8 | 1.8 |
| Sorbic acid | 0.8 | 0.8 | 0.8 |
| Sodium Hydroxide | 0.0–2.0 | 0.0–2.0 | 0.0–2.0 |
| LABRAFIL ® M2130 | 10 | 10 | 10 |

The individual ingredients of COL-2301 are well known and readily available from suppliers known in the industry.

Methylparaben and sorbic acid are preservatives, which may be substituted by any other known preservative, such as benzoic acid or propionic acid.

Carbomer 934P is a gel former, which may be substituted by other gel formers including, but not limited to, carbomer 974, carbomer 980, methylcellulose or propylcellulose.

Glycerin is a humectant; alternative humectants include, for example, propylene glycol and dipropylene glycol.

Light liquid paraffin is an emollient; alternatives include, for example, oils, such as mineral oil, peanut oil, castor oil, sesame oil, or corn oil.

Sodium hydroxide is a strong base used for purposes of controlling the pH level; other bases commonly used for that purpose may be substituted in its place.

LABRAFIL® M2130 is an optional agent that provides lubrication and acts as a whitener for the composition. Other known lubricants and/or whiteners may be used as a substitute.

General preparation involves hydration of the polymers, separate mixing of the polymer phase (water-soluble ingredients) and the oil phase (oil-soluble ingredients), heating and mixing of the two phases, and homogenization of the mixture. As an example, the polymer phase may be prepared by dissolving sorbic acid and methylparaben in purified water (which should contain approximately 3% of excess volume to account for evaporative losses), preferably at 75°–78° C. The mixture is then cooled generally to room temperature, and the polycarbophil and Carbomer 934P are added to the mixture. The polymers are hydrated by mixing for several hours, generally about 2–3 hours until a uniform, smooth, homogenous, lump-free, gel-like polymer mixture is obtained. When the polymers are completely hydrated, the β-adrenergic agonist is added and mixed in, until a homogeneous suspension is obtained.

The oil phase is generally prepared by melting together LABRAFIL® M2130, glycerin, and light liquid paraffin, and by heating the mixture to about 75 to 78° C. The mixture is then cooled to about 60° C. The polymer phase, described above, is meanwhile warmed to about the same temperature. The polymer phase is then added to the heated oil phase. The two phases are mixed thoroughly, producing a uniform, creamy white product. Sodium hydroxide is added, as needed, to produce a pH of about 2.5 to 4.5, generally about 4. After the mixture is cooled, it is de-aerated.

As will be apparent to those skilled in the art, the composition can be varied to affect certain properties. For example, the concentration of the bioadhesive polymer can be adjusted to provide greater or lesser bioadhesion. The viscosity can be varied by varying the pH or by changing the concentration of the polymer or gel former. The relative concentrations of the oils compared to the water can be varied to modulate the release rate of the terbutaline from the drug delivery system. The pH also can be varied as appropriate to affect the release rate or bioadhesiveness of the formulation.

Another preferred embodiment of the present inventive pharmaceutical composition is set forth in Table 2.

TABLE 2

Terbutaline 2 mg Tablet

| Component | % w/w | mg/tablet |
|---|---|---|
| Terbutaline (sulfate) | 2.222 | 2.000 |
| Magnesium stearate | 0.694 | 0.625 |
| Silicon dioxide | 1.000 | 0.900 |
| Talc | 1.189 | 1.070 |
| Hydroxypropylmethylcellulose | 20.845 | 18.760 |
| Polycarbophil | 2.483 | 2.235 |
| Carbomer 934P | 7.444 | 6.700 |
| Lactose | 46.267 | 41.640 |
| Corn starch | 17.856 | 16.070 |
| Final Weight | | 90.000 |

Another preferred embodiment of the present inventive pharmaceutical composition is set forth in Table 3.

TABLE 3

Terbutaline 4 mg Tablet

| Component | % w/w | mg/tablet |
|---|---|---|
| Terbutaline (sulfate) | 4.444 | 4.000 |
| Magnesium stearate | 0.694 | 0.625 |
| Silicon dioxide | 1.000 | 0.900 |
| Talc | 1.189 | 1.070 |
| Hydroxypropylmethylcellulose | 20.845 | 18.760 |
| Polycarbophil | 2.483 | 2.235 |
| Carbomer 934P | 7.444 | 6.700 |
| Lactose | 44.045 | 39.640 |
| Corn starch | 17.856 | 16.070 |
| Final Weight | | 90.000 |

Magnesium stearate and talc are lubricants; alternatives include calcium stearate, or stearic acid.

Silicon dioxide is a glidant; alternatives include colloidal silica, or cellulose.

Hydroxypropylmethylcellulose is a binder; alternatives include methylcellulose, carboxymethylcellulose, starch, glucose, lactose, or gelatin.

Lactose is used as a diluent; alternatives include mannitol, microcrystalline cellulose, compressible sugar, or dicalcium phosphate dihydrate.

Corn starch is a disintegrant; alternatives include methylcellulose, carboxymethylcellulose, guar gum, or agar.

A presently preferred method of manufacturing such bioadhesive tablets involves three steps as described below:

1. First step: manufacture of the granulate.

Hydroxypropylmethyl cellulose 15 000(=HPMC 15 000) is mixed with corn starch and lactose and in case of an active ingredient non sensitive to moisture the active is added. The mixture is wet with an aqueous solution of hydroxypropylmethyl cellulose 5 (=HPMC 5) and knead/granulated.

The granulate is dried in an oven under warm air (50⁻C) until moisture content is less than 2.5%

The dried granulate is broken with a stainless steel sieve oscillating granulator mesh size 1000 µm.

2. Second step: manufacture of the tableting mixture. Talc, silicon dioxide, magnesiun stearate, and for an active ingredient sensitive to moisture, the active ingredient is added. All are sieved through a sieving machine having an aperture size of 500 µm and then transferred into a free-fall mixer.

Addition of the granulate of step 1, followed by polycarbophil, Carbomer 934P and lactose. The whole is mixed until homogenous.

3. Third step: tableting

The tableting mixture is compressed into tablets by means of a rotative tableting machine equipped with punches 9 mm flat on the upper side and curved (r=9 mm) on the lower side both with beveled edge. The tablets are dedusted and packed.

As described above, an active ingredient that is not sensitive to moisture is preferably added during the manufacture of the granulate. However, alternatively, the active ingredient can be added during the second step after the granulate is dried and sieved. Also, as will be appreciated by one of ordinary skill in the art, this second method is particularly preferred when the active ingredient is sensitive to moisture.

In a presently preferred manufacturing process, the active ingredient is preferably protected from moisture. A wet granulation is made of lactose, corn starch and HPMC. Testosterone, polycarbophil, Carbomer 934P, talc and magnesium stearate are added dry for the final compression.

Furthermore, as will be appreciated by one of ordinary skill in the art following the teaching of the present application, the materials of construction can be varied to optimize the desired characteristics of the tablet. For example, by progressively decreasing the amount of lactose and corn starch and progressively increasing the amount of Carbomer 934P, the amount of time it takes a tablet to hydrate is progressively increased.

Methods of the Present Invention

The present invention contemplates a method of treating endometriosis, treating fertility, and/or improving fertility comprising administering a therapeutically effective amount of a composition comprising a β-adrenergic agonist and a pharmaceutically acceptable bioadhesive carrier locally to the vaginal mucosa of a patient in need thereof. These methods also can be practiced while avoiding normally-expected detrimental blood levels of the β-adrenergic agonist.

The vaginal route of administration with the specific bioadhesive polymer formulation discussed above is advantageous because it avoids first pass hepatic metabolism, which is typically significant for orally administered β-adrenergic agonists. Recently, this preferential or FIRST UTERINE PASS EFFECT® has been confirmed with [³H] labeled progesterone or terbutaline in an in vitro (ex-vivo) human uterine perfusion model. Therefore, vaginal administration of such a formulation will result in therapeutic concentrations of β-adrenergic agonist in the uterine and systemic concentrations low enough to avoid adverse reactions.

Preferably, about 0.5 g to 2.5 g of the inventive composition is administered vaginally. More preferably, about 1 g to 1.5 g of the composition is administered vaginally.

Further, the amount of β-adrenergic agonist contemplated for the present invention is preferably less than 1 mg to about 8 mg, and more preferably about 2 mg to 4 mg. Dosages of more than 8 mg are generally not recommended due to the side effects accompanying such levels. The composition is administered preferably once every 12 to 96 hours.

For vaginal administration, the inventive composition remains attached to the epithelial surfaces preferably for a period of at least about twenty-four to forty-eight hours. To determine whether the composition remains attached, vaginal pH is measured. Since the inventive composition acts as a buffering agent in a pH range of about 2.5 to about 4.5, pH measurements in this range, and preferably at 4.0 pH, should indicate the continued presence of the inventive composition.

All publications and patent applications mentioned herein are incorporated by reference. Reasonable variations, such as those that would occur to a skilled artisan, can be made herein without departing from the spirit and scope of the invention.

We claim:

1. A method of treating endometriosis, comprising administering a therapeutically effective amount of a composition comprising a β-adrenergic agonist and a pharmaceutically acceptable bioadhesive carrier locally to the vaginal mucosa of a patient in need thereof.

2. The method of claim 1, wherein the β-adrenergic agonist is terbutaline, and the composition is formulated to be administered in a dosage that delivers about 1 mg to about 8 mg of terbutaline.

3. The method of claim 2, wherein the composition is administered in a dosage that delivers about 2 mg to about 4 mg of terbutaline.

4. A method of treating endometriosis, comprising administering a therapeutically effective amount of a composition comprising a β-adrenergic agonist and a pharmaceutically acceptable bioadhesive carrier locally to the vaginal mucosa of a patient in need thereof, while avoiding detrimental blood levels of the β-adrenergic agonist.

5. The method of claim 4, wherein the β-adrenergic agonist is terbutaline.

6. The method of claim 5, wherein the bioadhesive carrier comprises a cross-linked water insoluble but water swellable polycarboxylic acid polymer.

7. The method of claim 6, wherein the polymer is polycarbophil.

8. The method of claim 3, wherein the composition is administered every 12 to 96 hours.

9. The method of claim 3, wherein the composition is administered twice weekly.

10. The method of claim 3, wherein the composition is administered in the form of a tablet.

11. The method of claim 3, wherein the composition is administered in the form of a gel or cream.

12. A method of treating infertility, or of improving fertility, by inhibiting retrograde contractions or by improving uterine contractility, comprising administering a therapeutically effective amount of a composition comprising a β-adrenergic agonist and a pharmaceutically acceptable bioadhesive carrier locally to the vaginal mucosa of a patient in need thereof, wherein the amount administered is sufficient to inhibit retrograde contractions or improve uterine contractility.

13. The method of claim 12, wherein the β-adrenergic agonist is terbutaline.

14. The method of claim 13, wherein the composition is formulated to be administered in a dosage that delivers about 1 mg to about 8 mg of terbutaline.

15. The method of claim 14, wherein the composition is administered in a dosage that delivers about 2 mg to about 4 mg of terbutaline.

16. The method of claim 15, wherein the bioadhesive carrier comprises a cross-linked water insoluble but water swellable polycarboxylic acid polymer.

17. The method of claim 16, wherein the polymer is polycarbophil.

18. The method of claim 12, wherein the composition is administered every 12 to 96 hours.

19. The method of claim 12, wherein the composition is administered twice weekly.

20. The method of claim 12, wherein the composition is administered in the form of a tablet.

21. The method of claim 12, wherein the composition is administered in the form of a gel or cream.

22. The method of claim 12, wherein detrimental blood levels of the β-adrenergic agonist are avoided.

23. The method of claim 12, wherein the infertility is associated with endometriosis.

* * * * *

UNITED STATES PATENT AND TRADEMARK OFFICE
CERTIFICATE OF CORRECTION

PATENT NO.   : 6,818,672 B1
DATED        : November 16, 2004
INVENTOR(S)  : Bologna et al.

It is certified that error appears in the above-identified patent and that said Letters Patent is hereby corrected as shown below:

Column 3,
Line 39, delete "Levine, et. al.," and insert -- Levine, et al., --.

Column 5,
Line 48, delete "fuirther" and insert -- further --.
Line 55, delete "water-insoluble. water-swellable," and insert -- water-insoluble, water-swellable --.

Column 6,
Line 42, delete "Convention. Inc.," and insert -- Convention, Inc., --.

Column 9,
Line 4, delete "(50⁻ C)" and inset -- (50° C) --.
Line 9, delete "magnesiun" and insert -- magnesium --.

Signed and Sealed this

Twenty-seventh Day of September, 2005

JON W. DUDAS
*Director of the United States Patent and Trademark Office*